US006792954B2

United States Patent
Cannell et al.

(10) Patent No.: US 6,792,954 B2
(45) Date of Patent: *Sep. 21, 2004

(54) HAIR RELAXER COMPOSITIONS UTILIZING CATION EXCHANGE COMPOSITIONS

(75) Inventors: David W. Cannell, Plainfield, NJ (US); Nghi Van Nguyen, Edison, NJ (US)

(73) Assignee: L'Oreal (FR)

( * ) Notice: Subject to any disclaimer, the term of this patent is extended or adjusted under 35 U.S.C. 154(b) by 68 days.

This patent is subject to a terminal disclaimer.

(21) Appl. No.: 10/214,942

(22) Filed: Aug. 9, 2002

(65) Prior Publication Data

US 2003/0049221 A1 Mar. 13, 2003

Related U.S. Application Data

(63) Continuation of application No. 09/717,206, filed on Nov. 22, 2000, now Pat. No. 6,435,193.

(51) Int. Cl.$^7$ .................................................. A45C 7/04
(52) U.S. Cl. ....................................... 132/203; 424/70.4
(58) Field of Search ................................. 132/202, 203, 132/204, 205, 206, 207; 424/70.2, 70.4

(56) References Cited

U.S. PATENT DOCUMENTS 5,376,364 A   12/1994   Darkwa et al.

FOREIGN PATENT DOCUMENTS

| DE | 28 23 243 | 11/1979 |
| WO | WO 97/07775 | 3/1997 |
| WO | WO 01/64171 A2 | 9/2001 |

*Primary Examiner*—Todd E. Manahan
(74) *Attorney, Agent, or Firm*—Finnegan, Henderson, Farabow, Garrett & Dunner, L.L.P.

(57) ABSTRACT

A composition for lanthionizing keratin fibers comprising at least one multivalent metal hydroxide and at least one cation exchange composition. The invention is also drawn to a method for lanthionizing keratin fibers to achieve relaxation of the keratinous fibers.

64 Claims, No Drawings

HAIR RELAXER COMPOSITIONS UTILIZING CATION EXCHANGE COMPOSITIONS

This is a continuation of application Ser. No. 09/717,206 filed Nov. 22, 2000, now U.S. Pat. No. 6,435, 193 which is incorporated herein by reference.

The present invention relates to compositions and methods for lanthionizing keratin fibers using a combination of at least one multivalent metal hydroxide and at least one cation exchange composition. The at least one cation exchange composition can dissociate the at least one multivalent metal hydroxide in sufficient quantity to effect lanthionization of the keratin fibers. In one embodiment, the process of lanthionizing keratin fibers results in relaxed or straightened hair.

Straightening or relaxing the curls of very curly hair may increase the manageability and the ease of styling such hair. In today's market, there is an increasing demand for hair care products referred to as "hair relaxers" which can relax or straighten naturally curly or kinky hair. Hair relaxers may either be applied in a hair salon by a professional or in the home by the individual consumer.

Hair fiber is a keratinous material, which is comprised of proteins (polypeptides). Many of the polypeptides in hair fibers are bonded together by disulfide bonds (—S—S—). A disulfide bond may be formed from the reaction of the two sulfhydryl groups (—SH), one on each of two cysteine residues, which results in the formation of a cystine residue. While there may be other types of bonds between the polypeptides in hair fibers, such as ionic salt bonds, the permanent curling and shape of the hair is essentially dependent on the disulfide bonds of cystine residues.

Generally, hair relaxing processes are chemical processes which may alter the aforementioned disulfide bonds between polypeptides in hair fibers and may form lanthionine $[S(CH_2CHNH_2COOH)_2]$. Thus, the term "lanthionizing" is used when one skilled in the art refers to the relaxing or straightening of keratin fibers by hydroxide ions.

For example, hair fibers may be relaxed or straightened by disrupting the disulfide bonds of the hair fibers with an alkaline agent or with a reducing agent. The chemical disruption of disulfide bonds with an alkaline agent is generally combined with mechanical straightening of the hair, such as combing, and straightening generally occurs due to changes in the relative positions of opposing polypeptide chains within the hair fiber. This reaction is generally terminated by rinsing and/or application of a neutralizing composition.

The reaction with the alkaline agent is normally initiated by hydroxide ions. Not to be limited by theory, there are two reaction sequences that are predominantly used in the art to explain the disruption of the disulfide bonds in hair fibers by hydroxide ions. Both of these reaction sequences result in lanthionine residue formation. One reaction sequence comprises a bimolecular nucleophilic substitution reaction wherein a hydroxide ion directly attacks the disulfide linkage of a cystine residue. The result is the formation of lanthionine and HOS. See Zviak, C., *The Science of Hair Care*, 185–186 (1986). The second reaction sequence comprises at least one β-elimination reaction initiated by the nucleophilic attack of a hydroxide ion on a hydrogen atom bonded to a carbon atom that is in the β-position with respect to the disulfide bond of a cystine residue. Id. The result is the formation of a dehydroalanine residue. The dehydroalanine residue then reacts with either the thio group of a cysteine residue or the amino group of alanine residue to form lanthionine or lysinoalanine, respectively. Regardless of the reaction mechanism, hair relaxing processes proceed via the release of hydroxide ions that can penetrate the hair fiber and which may transform cystine residues to lanthionine residues.

Most frequently, relaxing compositions are in the form of gels or emulsions that contain varying proportions of strong water-soluble bases, such as sodium hydroxide (NaOH), or of compositions that contain slightly-soluble metal hydroxides, such as calcium hydroxide ($Ca(OH)_2$), which can be converted in situ to soluble bases, such as guanidine hydroxide. Traditionally, the two main hair relaxing technologies used in the hair care industry for generating hydroxide ions are referred to as "lye" relaxers (lye=sodium hydroxide) and "no lye" relaxers. The "lye" relaxers generally comprise sodium hydroxide in a concentration generally ranging from 1.5% to 2.5% (0.38 M–0.63 M) depending on the carrier used, the condition of the hair fibers, and the desired length of the relaxation process. Sodium hydroxide may be extremely effective in straightening hair fibers but may result in a decrease in the strength of the hair fibers and, in some cases, partial or total loss of hair due to hair fiber breakage.

While "no lye" relaxers may not contain lye, they may nonetheless rely on the soluble hydroxides of inorganic metals, such as potassium hydroxide and lithium hydroxide. Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

Guanidine carbonate and calcium hydroxide, however, may create a different set of problems. The insoluble byproduct, $CaCO_3$, can leave a white residue or unattractive "whitening" or "ashing." This residue remains in the hair since divalent metals such as calcium have a relatively good affinity for keratin. A decalcifying shampoo may be subsequently needed to remove the ashing.

Thus, there is still a need for a process to relax keratin fibers that has the advantages of using a slightly-soluble metal hydroxide, such as $Ca(OH)_2$, but which reduces or eliminates the problem of ashing caused by insoluble byproducts, such as $CaCO_3$.

To achieve at least one of these and other advantages, and in accordance with the purpose of the invention as embodied and broadly described herein, the present invention, in one aspect, provides a composition for lanthionizing keratin fibers comprising at least one multivalent metal hydroxide and at least one cation exchange composition. According to the present invention, at least one cation exchange composition may be chosen from silicates. The at least one multivalent metal hydroxide may be chosen from, for example, calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

The present invention is also directed to a method for lanthionizing keratin fibers to achieve relaxation of the keratin fibers by generating hydroxide ions in an ionizing solvent comprising combining at least one multivalent metal hydroxide and at least one activating composition, wherein the at least one activating composition comprises at least one cation exchange composition, to generate hydroxide ions; and applying a composition comprising the generated hydroxide ions to keratin fibers for a sufficient period of time to lanthionize the keratin fibers. Lanthionization is terminated when the desired level of relaxation of the keratin fibers has been reached. The at least one multivalent metal hydroxide may be added to a composition comprising the at least one cation exchange composition or vice versa.

The invention also provides for a multicomponent kit for lanthionizing keratin fibers, wherein the kit comprises at least two separate compartments. One compartment of the kit comprises a composition for generating hydroxide ions that comprises at least one multivalent metal hydroxide while the other compartment of the kit comprises at least one activating composition comprising at least one cation exchange composition for generating hydroxide ions.

It is to be understood that both the foregoing general description and the following detailed description are exemplary and explanatory only and are not restrictive of the invention as claimed.

Reference will now be made in detail to exemplary embodiments of the present invention. Not to be limited as to theory, the lanthionization of keratin fibers is driven by the release of hydroxide ions, which disrupt the disulfide bonds of cystine residues in the fibers. The compositions of the present invention may offer at least one advantage over traditional "lye" and "no lye" hair relaxers by providing a novel way of generating hydroxide ions from multivalent metal hydroxides while still being effective to relax and/or straighten the hair.

As described above, the hair relaxing compositions of the prior art utilized soluble or slightly soluble metal hydroxides. Slightly soluble metal hydroxides, including most divalent metal hydroxides, may not be soluble enough in water to generate a sufficient concentration of hydroxide ions to effect lanthionization of keratin fibers. This hydrolysis reaction of divalent metal hydroxides can be represented by the following reaction scheme, in which the equilibrium favors the left side of the reaction:

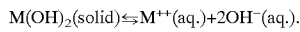

$$M(OH)_2(\text{solid}) \rightleftharpoons M^{++}(\text{aq.}) + 2OH^-(\text{aq.}).$$

In traditional relaxers containing slightly soluble metal hydroxides, the equilibrium was normally pushed to the right, and therefore the reaction was driven to completion by the precipitation of $M^{++}$ in the form of an insoluble compound such as $CaCO_3$.

The compositions of the present invention, however, utilize cation exchange compositions such as silicates. Not to be limited as to theory, it is believed that the cation exchange composition participates in the lanthionizing process through an ion exchange mechanism. It is believed that the reversible ion exchange reaction involves the interchange of the multivalent metal ions of the at least one multivalent metal hydroxide with ions of the at least one cation exchange composition. This reaction thereby releases hydroxide ions. In other words, the exchange of $M^{++}$, in the case of divalent metal hydroxides, to the at least one cation exchange composition shifts the equilibrium of the above reaction to the right such that the net effect is that hydroxide ions are liberated from the insoluble or slightly-soluble at least one multivalent metal hydroxide. This process may thereby generate a high enough concentration of hydroxide ions to effect lanthionization of keratin fibers without relying on the precipitation of $M^{++}$, for example, in the form of an insoluble precipitate such as $CaCO_3$.

Any cation exchange composition or combination of cation exchange compositions which is effective in participating in the lanthionizing process may be used according to the present invention, including, but not limited to, silicates and mixtures of silicates. In one embodiment, the at least one cation exchange composition is a clay.

For example, suitable silicates may be chosen from aluminum silicates and silicates of alkali metals such as analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, phillipsite, and aluminosilicate. Non-limiting examples of alkali metals are sodium, lithium, potassium and mixtures of all of the foregoing. In one embodiment the silicate is a zeolite, while in another embodiment, the silicate is a zeolite clay.

The present invention is also directed to simple screening tests for determining the applicability of particular cation exchange composition for use in the lanthionizing compositions of the present invention. By titrating a suspension of at least one multivalent metal hydroxide, such as $Ca(OH)_2$, with the cation exchange composition of interest, the exchange properties of the cation exchange composition may be observed. For example, if the solution reaches a pH sufficient for lanthionizing keratin fibers, then the particular cation exchange composition is a good candidate for use in the compositions of the present invention. However, even if the pH reached is not sufficient, the particular cation exchange composition may still be a good candidate if the presence of another ingredient, such as at least one complexing agent, allows lanthionization to occur.

The ability of an cation exchange composition to exchange or take up a metal ion such as calcium is sometimes referred to as the Calcium Exchange Capacity, and is normally expressed as mg of $CaCO_3$ per gram of cation exchange composition. One of skill in the art may choose an cation exchange composition or combination of cation exchange compositions based on the Calcium Exchange Capacity of the resin and the application envisaged. The skilled artisan may also choose to add other components, such as at least one complexing agent as described below, depending on the Calcium Exchange Capacity of the cation exchange compositions of interest and the application envisaged.

In one embodiment, the cation exchange composition is present in an amount ranging from 1% to 50% relative to the total weight of the composition.

The compositions of the present invention may also include at least one complexing agent effective for dissociating the at least one multivalent metal hydroxide in a sufficient quantity to effect lanthionization of keratin fibers. The at least one complexing agent may be an agent, such as a chelating agent or a sequestering agent, that leads to a partial or full dissociation of the at least one multivalent metal hydroxide. The at least one complexing agent may chelate, sequester or otherwise tie up the metal ion of the at least one multivalent metal hydroxide, allowing more hydroxide ions to be liberated. Of course, the at least one complexing agent may do both. In any event, the net effect of the use of at least one complexing agent in accord with the present invention is the generation of enough hydroxide ions to effect lanthionization of keratin fibers without relying on the precipitation of the multivalent metal ion, such as $Ca^{++}$ in the form of $CaCO_3$.

The at least one complexing agent and the multivalent metal may form a complex that, in most cases, has stronger interactions between the at least one complexing agent and the multivalent metal ion than the interactions between the multivalent metal and the hydroxide ion. As a result, the at least one complexing agent effectively removes the multivalent metal from the reaction medium and allows the equilibrium to be shifted to the right.

Thus, the at least one cation exchange composition can be used in combination with at least one complexing agent to modulate or control the rate of release of hydroxide ions from the at least one multivalent metal hydroxide, thereby producing a mixed composition for gentler relaxing and/or partial relaxing. A mixture of at least one complexing agent and at least one cation exchange composition may increase relaxing efficiency.

In a multicomponent kit, for example, the at least one cation exchange composition may be formulated with the component comprising at least one multivalent metal hydroxide or with the component comprising at least one complexing agent or itself may be a third component that is combined with one or both of the component comprising at least one multivalent metal hydroxide and the component comprising at least one complexing agent.

The at least one complexing agent of the present invention includes, but is not limited to, chelating agents and sequestering agents. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion, such as $Co^{2+}$, $Ni^{2+}$, $Cu^{2+}$, $Ca^{2+}$ or $Zn^{2+}$, is attached by coordinate links to two or more nonmetal atoms, i.e., ligands, in the same molecule. Non-limiting examples of common chelating agents include ethylenediaminetetraacetic acid (EDTA), nitrilotriacetic acid, and ethylenegylcol-bis($\beta$-amino-ethyl ether)-N,N-tetraacetic acid.

Sequestering agents may be any material that prevents at least one ion from exhibiting its usual properties due to close combination with that material. Id. at 991. Certain phosphates, for example, form a coordination complex with metal ions in solution so that the usual precipitation reactions may be prevented. Id. For example, calcium soap precipitates are not produced from hard water treated with certain phosphates or metaphosphates. Id. Other non-limiting examples of sequestering agents include hydroxy carboxylic acids, such as gluconic acid, citric acid and tartaric acid. Id.

As previously mentioned, the at least one complexing agent can be chosen from chelating agents and sequestering agents. Non-limiting examples of chelating agents and sequestering agents include amino acids and crown ethers. In one embodiment, the at least one complexing agent is chosen from amino acids, such as monosodium glutamate, which is a known calcium chelator.

The at least one complexing agent may also be chosen from phosphates demonstrating chelating and/or sequestering properties and silicates demonstrating chelating and/or sequestering properties. Non-limiting examples of phosphates demonstrating chelating and/or sequestering properties include tripotassium phosphate, and trisodium phosphate. Non-limiting examples of silicates demonstrating chelating and/or sequestering properties include disodium silicate and of dipotassium silicate.

Other non-limiting examples of the at least one complexing agent that may be useful in the practice of the invention include organic acids and salts thereof. The cations that may be used to form the salts of organic acids of the present invention may be chosen from organic cations and inorganic cations. In one embodiment, the inorganic cations are chosen from potassium, sodium and lithium.

In another embodiment, the at least one complexing agent is chosen from mono-hydroxycarboxylic acids, dihydroxycarboxylic acids, polyhydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids and polyaminophosphonic acids.

In a further embodiment, the at least one complexing agent is chosen from ethylene diamine tetraacetic acid (EDTA), -(hydroxyethyl) ethylene diamine triacetic acid, aminotrimethylene phosphonic acid, diethylenetriaminepentaacetatic acid, lauroyl ethylene diamine triacetic acid, nitrilotriacetic acid, iminodisuccinic acid, tartaric acid, citric acid, N-2-hydroxyethyliminodiacetic acid and salts of any of the foregoing.

In a further embodiment, the at least one complexing agent is chosen from a salt of EDTA, such as sodium EDTA, lithium EDTA, potassium EDTA and guanidine EDTA. EDTA has a strong calcium binding constant over a wide range of pH. For example, tetrasodium EDTA generally solubilizes calcium hydroxide in aqueous media to give a clear solution. The use of at least one complexing agent, such as tetrasodium EDTA, that solubilizes the multivalent metal ion of the at least one multivalent metal hydroxide may offer the benefit of no "ashing." However, the use of one or more complexing agents that do not completely solubilize the multivalent metal ion but only form slightly-soluble or sparingly-soluble complexing agent-multivalent metal ion complexes is also within the practice of the invention.

In another embodiment, the at least one complexing agent may comprise at least one "soft" entity chosen from "soft" bases and "soft" cations, and at least one anion chosen from chelating anions and sequestering anions. Non-limiting examples of "soft" cations include organic cations such as guanidine. Non-limiting examples of "soft" bases include amines such as monoethanolamine, diethanolamine and triethanolamine. Such a combination of at least one "soft" entity and at least one anion may be effective if the "soft" entity exists at a high enough pH to achieve straightening or relaxing of the hair fibers. For example, amino acids such as arginine may be used to neutralize EDTA to make a "soft" base/strong chelator pair.

Depending on the nature of the at least one complexing agent, the solubility in of the complex formed between the at least one complexing agent and the multivalent metal ion of the at least one multivalent metal hydroxide in the reaction medium may vary. In one embodiment, the at least one complexing agent-multivalent metal ion complex is considered by one of ordinary skill in the art to be soluble in the reaction medium. In another embodiment, a composition of the invention provides for an at least one complexing agent-multivalent metal ion complex having a solubility in water of greater than 0.03% at 25° C. and at a pH of 7.0, such as greater than 1% at 25° C. and at a pH of 7.0.

The present invention is also directed to simple screening tests for determining the applicability of a particular complexing agent for use in the lanthionizing compositions of the present invention. This screening test is essentially the same test as that described above for determining the applicability of a particular cation exchange composition in the present invention. In the present test, a suspension of at least one multivalent metal hydroxide, such as $Ca(OH)_2$, is titrated with the complexing agent of interest, and the chelating and/or sequestering properties of the particular complexing agent may be observed. For example, if the solution reaches a pH sufficient for lanthionizing keratin fibers, then the complexing agent is a good candidate for use in the compositions of the present invention.

The at least one cation exchange composition and the at least one complexing agent of the present invention may offer one or more of the following benefits: compatibility with keratin conditioning ingredients (polyquaternium compounds, polymers, proteins, alkylquaternary ammonia compounds, silicones, etc.); capability to be stored as a stable mixture, that is, the formation of a stable mixture of at least one complexing agent and at least one multivalent metal hydroxide that can be stored for later use, an advantage which is not possible with compositions that result in the unstable guanidinium hydroxide; and the absence of a precipitation by-product and/or the absence of the need to apply a decalcifying shampoo after relaxing.

As one of ordinary skill in the art would recognize, mixtures of complexing agents including mixtures of at least one chelating agent and at least one sequestering agent are also within the practice of the invention. In one embodiment, a less active chelating agent, such as pentasodium aminotrimethylene phosphonate, may be mixed with a more active chelating agent, such as EDTA, to achieve a desired lanthionization of keratin fibers at a slower rate.

The at least one multivalent metal hydroxide useful in the present invention may be chosen from multivalent metal hydroxides which are an effective source of hydroxide ions for lanthionizing keratin fibers when combined with at least one complexing agent. In one embodiment, the at least one multivalent metal hydroxide is chosen from insoluble alkali metal hydroxides and slightly soluble metal hydroxide including but not limited to, calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

The at least one multivalent metal hydroxide, for example, may be present in an amount ranging from 1% to 10% relative to the total weight of the composition.

The compositions of the present invention may be provided as one-part compositions comprising at least one multivalent metal hydroxide, at least one cation exchange composition, and, optionally, at least one complexing agent. Alternatively, the compositions may be provided in the form of a multicomponent kit. According to the present invention, the multicomponent kit for lanthionizing keratin fibers may comprise at least two separate compartments. A first compartment of the kit can comprise a first composition comprising at least one multivalent metal hydroxide. This first composition may be in the form of an emulsion, solution, suspension, gel or paste. A second compartment of the kit can comprise at least one activating composition comprising at least one cation exchange composition for generating hydroxide ions and, optionally, at least one complexing agent that is effective for dissociating the at least one multivalent metal hydroxide in sufficient quantity to effect lanthionization of keratin fibers. This activating composition may be in the form of an emulsion, suspension, solution, gel or paste. The skilled artisan, based on the stability of the composition and the application envisaged, will be able to determine how the composition and/or multicomponent compositions should be stored and mixed.

In one embodiment, one of the at least two components of the multicomponent kit comprises an amount of an ionizing solvent, such as water, sufficient to ensure that, upon mixing, enough of the generated hydroxide ions remain soluble to effect lanthionization of keratin fibers.

The present invention is also directed to methods for lanthionizing keratin fibers in order to achieve relaxation of the keratin fibers. The methods of the present invention comprise generating hydroxide ions in an ionizing solvent comprising combining at least one activating composition and at least one multivalent metal hydroxide. The at least one activating composition comprises at least one cation exchange composition. The at least one activating composition may further comprise at least one complexing agent effective for dissociating the at least one multivalent metal hydroxide in sufficient quantity to effect lanthionization of keratin fibers. A composition comprising the generated hydroxide ions can thereby be formed and the composition applied to keratin fibers for a sufficient period of time to lanthionize the keratin fibers. The lanthionization can be terminated when a desired level of relaxation of the keratin fibers is reached.

The ionizing solvents may be chosen from solvents that lower the ionic bonding forces in the solute molecules enough to cause separation of their constituent ions. In one embodiment, the ionizing solvent is chosen from water and dimethyl sulfoxide (DMSO).

The method also encompasses forming the hydroxide ions in situ, i.e., while on the keratin fibers, by combining at least one multivalent metal hydroxide and at least one activating composition in the presence of the keratin fibers.

The invention will be illustrated by, but is not intended to be limited to, the following examples.

EXAMPLE 1

The Ability of an Cation Exchange Composition to Produce Soluble Hydroxide

An cation exchange composition, Sodium Aluminum Silicate (Advera™ 401 Na-A Zeolite Powder or Zeolite A from Advera Specialty Zeolites, Valley Forge, Pa.), was used to demonstrate the ability of a cation exchange composition to exchange calcium with a multivalent metal hydroxide and thereby generate sufficient hydroxide ions for use in lanthionization.

The Calcium Exchange Capacity of Zeolite A is reported from the manufacturer to be 275 mg $CaCO_3$/g Zeolite A (anhydrous base). In other words, 1 g of anhydrous Zeolite A will exchange with 275 mg of $Ca^{2+}$ as $CaCO_3$ or 2.75 mmoles of $Ca^{2+}$. Therefore, when calcium hydroxide is used instead of $CaCO_3$, it is expected that 1 g of anhydrous Zeolite A will generate 5.5 mmoles of hydroxide ions.

The ability of the cation exchange composition Zeolite A to exchange calcium under various pHs was also studied. Zeolite powder was added to a stirring solution of $CaCl_2$ at pH 8.4, 10.1, and 12.2. A Calcium Ion Activity Electrode was then used to monitor the decrease in calcium following addition of the cation exchange composition. The results in Table 1 are reported as the Calcium Exchange Rate (mg $CaCO_3$/g Zeolite), which is measured 2 minutes after addition of the cation exchange composition and Calcium Exchange Capacity (mg $CaCO_3$/g Zeolite), which is measured 15 minutes after addition of the cation exchange composition.

|                                              | pH = 8.4 | pH = 10.1 | pH = 12.2 |
|----------------------------------------------|----------|-----------|-----------|
| Calcium Exchange Rate (mg CaCO$_3$/g Zeolite) | 102      | 105       | 131       |
| Calcium Exchange Capacity (mg CaCO$_3$/g Zeolite) | 165  | 186       | 233       |

The data demonstrate that the Calcium Exchange Rate and the Calcium Exchange Capacity of the cation exchange composition, Zeolite A, increased with pH of the medium, i.e., the higher the pH, the greater the exchange of calcium. This shows that cation exchange compositions can be used alone or in conjunction with chelating agents to generate hydroxide ions from calcium hydroxide and other metal hydroxides. The process may then be applied to hair fibers to effect lanthionization.

EXAMPLE 2

Hair Relaxing Compositions Comprising Zeolite Clay and a Complexing Agent.

A two component hair relaxing composition was prepared. The first component, a cream composition containing the complexing agent tetrasodium EDTA was prepared as follows:

| Materials                                | % w/w |
|------------------------------------------|-------|
| Cetyl alcohol                            | 1.0   |
| Steareth-2                               | 0.5   |
| Steareth-10                              | 2.5   |
| Mineral Oil                              | 15.0  |
| Petrolatum                               | 5.5   |
| Cetearyl alcohol and Cetearyl Phosphate  | 7.5   |
| Propylene Glycol                         | 3.0   |
| Tetrasodium EDTA                         | 30.5  |
| Water                                    | 34.5  |

Four different samples of a second composition were then prepared containing 0.3 g Ca(OH)$_2$, 2 g of water, and the amount of Zeolite clay (Sodium Aluminosilicate from The PQ Corporation P.O. Box 840, Valley Forge, Pa. 19482) shown in Table 2. The second composition was then added to 1.8 g of the complexing agent cream.

Procedure for Measuring Relaxing Efficiency

After mixing for 3 minutes, the mixture was applied to a natural kinky hair swatch that was stretched and taped in a straight configuration. The relaxer mixture was worked into the hair swatch for 5 minutes and the treated hair swatch was allowed to stand at ambient temperature for another 15 minutes. The hair swatch was rinsed and shampooed then placed in the humidity chamber at 90% Relative Humidity for 24 hours. The % Relaxing Efficiency (% RE) is defined as:

$$\%RE = (L_f/L_t) \times 100$$

where $L_f$=Length of the relaxed hair after 24 hours at 90%RH
$L_t$=Length of the hair at the straight configuration.

The relaxing efficiency for each sample is shown in Table 2.

The results indicate that the addition of Zeolite clay to the hair relaxing composition improved the composition's relaxing efficiency.

TABLE 2

Effects of Adding Zeolite Clay to Hair Relaxing Compositions

| g of Zeolite Clay | % Relaxing Efficiency |
|-------------------|-----------------------|
| 0                 | 64                    |
| 0.2               | 71                    |
| 0.5               | 79                    |
| 1                 | 79                    |

It will be apparent to those skilled in the art that various modifications and variations can be made in the compositions and methods of the present invention without departing from the spirit or scope of the invention. Thus, it is intended that the present description cover the modifications and variations of this invention provided that they come within scope of the appended claims and their equivalents.

What is claimed is:

1. A composition for lanthionizing keratin fibers comprising water, at least one multivalent metal hydroxide, and at least one cation exchange composition, wherein said at least one cation exchange composition is chosen from zeolites.

2. A composition for lanthionizing keratin fibers according to claim 1, wherein said keratin fibers are human hair.

3. A composition for lanthionizing keratin fibers according to claim 1, wherein said at least one multivalent metal hydroxide is in solution.

4. A composition for lanthionizing keratin fibers according to claim 1, wherein said at least one multivalent metal hydroxide is present in an amount ranging from 1% to 10% relative to the total weight of the composition.

5. A composition for lanthionizing keratin fibers according to claim 1, wherein said at least one multivalent metal hydroxide is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

6. A composition for lanthionizing keratin fibers according to claim 5, wherein said at least one multivalent metal hydroxide is calcium hydroxide.

7. A composition for lanthionizing keratin fibers according to claim 1, wherein said zeolites are zeolite clays.

8. A composition for lanthionizing keratin fibers according to claim 1, wherein said zeolites are chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, and phillipsite.

9. A composition for lanthionizing keratin fibers according to claim 1, wherein said at least one cation exchange composition is present in an amount ranging from 1% to 50% relative to the total weight of said composition.

10. A composition for lanthionizing keratin fibers according to claim 1, wherein said at least one activating composition further comprises at least one complexing agent effective for dissociating said at least one multivalent metal hydroxide.

11. A composition for lanthionizing keratin fibers according to claim 10, wherein said at least one complexing agent is chosen from chelating agents and sequestering agents.

12. A composition for lanthionizing keratin fibers according to claim 11, wherein said chelating agents are chosen from ethylene-diaminetetraacetic acid (EDTA), nitrilotriacetic acid, and ethyleneglycol-bis(-amino-ethyl ether)-N,N-tetraacetic acid.

13. A composition for lanthionizing keratin fibers according to claim 12, wherein said ethylene-diaminetetraacetic acid (EDTA) is chosen from a salt of EDTA.

14. A composition for lanthionizing keratin fibers according to claim 10, wherein said at least one complexing agent is chosen from amino acids and crown ethers.

15. A composition for lanthionizing keratin fibers according to claim 10, wherein said at least one complexing agent is chosen from phosphates demonstrating chelating and/or sequestering properties and silicates demonstrating chelating and/or sequestering properties.

16. A composition for lanthionizing keratin fibers according to claim 10, wherein said at least one complexing agent is chosen from organic acids and salts thereof.

17. A composition for lanthionizing keratin fibers according to claim 10, wherein a complex is formed between said at least one complexing agent and at least one multivalent metal ion of said at least one multivalent metal hydroxide and wherein said complex has a solubility in water of greater than 0.03% at 25° C. and a pH of 7.0.

18. A composition for lanthionizing keratin fibers according to claim 17, wherein a complex is formed between said at least one complexing agent and at least one multivalent metal ion of said at least one multivalent metal hydroxide and wherein said complex has a solubility in water of greater than 1% at 25° C. and a pH of 7.0.

19. A composition for lanthionizing keratin fibers according to claim 10, wherein said dissociation of said at least one multivalent metal hydroxide is a partial dissociation.

20. A multicomponent kit for lanthionizing keratin fibers comprising:
   (a) a first compartment comprising a first composition,
   (b) a second compartment comprising a second composition,
   wherein said first compartment comprises a composition comprising at least one multivalent metal hydroxide;
   wherein said second compartment comprises at least one activating composition comprising at least one cation exchange composition for generating hydroxide ions; and
   wherein at least one of said first composition and said second composition further comprises water.

21. A multicomponent kit for lanthionizing keratin fibers according to claim 20, wherein said at least one activating composition further comprises at least one complexing agent effective for dissociating said at least one multivalent metal hydroxide.

22. A multicomponet kit for lanthionizing keratin fibers according to claim 21, wherein said at least one complexing agent is chosen from chelating agents and sequestering agents.

23. A multicomponent kit for lanthionizing keratin fibers according to claim 22, wherein said chelating agents are chosen from ethylene-diaminetetraacetic acid (EDTA), nitrilotriacetic acid, and ethyleneglycol-bis (β-amino-ethyl ether)-N,N-tetraacetic acid.

24. A multicomponent kit for lanthionizing keratin fibers according to claim 23, wherein said ethylene-diaminetetraacetic acid (EDTA) is chosen from a salt of EDTA.

25. A multicomponent kit for lanthionizing keratin fibers according to claim 24, wherein said salt of EDTA is chosen from sodium EDTA, lithium EDTA, potassium EDTA and guanidine EDTA.

26. A multicomponent kit for lanthionizing keratin fibers according to claim 21, wherein said at least one complexing agent is chosen from amino acids and crown ethers.

27. A multicomponent kit for lanthionizing keratin fibers according to claim 26, wherein said amino acids is monosodium glutamate.

28. A multicomponent kit for lanthionizing keratin fibers according to claim 21, wherein said at least one complexing agent is chosen from phosphates demonstrating chelating and/or sequestering properties and silicates demonstrating chelating and/or sequestering properties.

29. A multicomponent kit for lanthionizing keratin fibers according to claim 28, wherein said phosphates are chosen from tripotassium phosphate and trisodium phosphate.

30. A multicomponent kit for lanthionizing keratin fibers according to claim 28, wherein said silicates are chosen from disodium silicate and dipotassium silicate.

31. A multicomponent kit for lanthionizing keratin fibers according to claim 21, wherein said at least one complexing agent is chosen from organic acids and salts thereof.

32. A multicomponent kit for lanthionizing keratin fibers according to claim 31, wherein said organic acids are chosen from amino-carboxylic acids, hydroxy-carboxylic acids, amino-sulfonic acids, hydroxy-sulfonic acids, amino-phosphonic acids and hydroxy-phosphonic acids.

33. A multicomponent kit for lanthionizing keratin fibers according to claim 32, wherein said hydroxy-carboxylic acids are chosen from gluconic acid, citric acid and tartaric acid.

34. A multicomponent kit for lanthionizing keratin fibers according to claim 31, wherein said salts are chosen from organic cations and inorganic cations.

35. A multicomponent kit for lanthionizing keratin fibers according to claim 34, wherein said inorganic cations are chosen from potassium, sodium and lithium.

36. A multicomponent kit for lanthionizing keratin fibers according to claim 31, wherein said organic acids are chosen from, NB(hydroxyethyl) ethylene diamine triacetic acid, aminotrimethylene phosphonic acid, diethylenetriamine-pentaacetic acid, lauroyl ethylene diamine triacetic acid, iminodisuccinic acid, tartaric acid, citric acid, and N-2-hydroxyethyliminodiacetic acid.

37. A multicomponent kit for lanthionizing keratin fibers according to claim 21, wherein said at least one complexing agent comprises at least one soft entity chosen from soft bases and soft cations, and at least one anion chosen from chelating anions and sequestering anions.

38. A multicomponent kit for lanthionizing keratin fibers according to claim 37, wherein said soft cations are chosen from organic cations.

39. A multicomponent kit for lanthionizing keratin fibers according to claim 37, wherein said soft bases are chosen from monoethanolamine, diethanolamine and triethanolamine.

40. A multicomponent kit for lanthionizing keratin fibers according to claim 21, wherein a complex is formed between said at least one complexing agent and at least one multivalent metal ion of said at least one multivalent metal hydroxide and wherein said complex has a solubility in water of greater than 0.03% at 25° C. and a pH of 7.0.

41. A multicomponent kit for lanthionizing keratin fibers according to claim 40, wherein a complex is formed between said at least one complexing agent and at least one multivalent metal ion of said at least one multivalent metal hydroxide and wherein said complex has a solubility in water of greater than 1% at 25° C. and a pH of 7.0.

42. A multicomponent kit for lanthionizing keratin fibers according to claim 21, wherein said dissociation of said at least one multivalent metal hydroxide is a partial dissociation.

43. A multicomponent kit for lanthionizing keratin fibers according to claim 20, wherein at least one of said first composition and said second composition is each independently in a form chosen from creams, emulsions, and gels.

44. A multicomponent kit for lanthionizing keratin fibers according to claim 20, wherein said keratin fibers are human keratin fibers.

45. A multicomponent kit for lanthionizing keratin fibers according to claim 44, wherein said human keratin fibers are hair.

46. A multicomponent kit for lanthionizing keratin fibers according to claim 20, wherein said at least one multivalent metal hydroxide is in solution.

47. A multicomponent kit for lanthionizing keratin fibers according to claim 20, wherein at least one cation exchange composition is not in solution.

48. A multicomponent kit for lanthionizing keratin fibers according to claim 20, wherein said at least one multivalent metal hydroxide is present in an amount ranging from 1% to 10% relative to the total weight of the composition formed upon mixing said first composition and said second composition.

49. A multicomponent kit for lanthionizing keratin fibers according to claim 20, wherein said at least one multivalent metal hydroxide is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide.

50. A multicomponent kit for lanthionizing keratin fibers according to claim 49, wherein said at least one multivalent metal hydroxide is calcium hydroxide.

51. A multicomponent kit for lanthionizing keratin fibers according to claim 20, wherein said at least one cation exchange composition is chosen from silicates.

52. A multicomponent kit for lanthionizing keratin fibers according to claim 51, wherein said silicates are chosen from zeolites.

53. A multicomponent kit for lanthionizing keratin fibers according to claim 52, wherein said zeolites are zeolite clays.

54. A multicomponent kit for lanthionizing keratin fibers according to claim 51, wherein said silicates are chosen from aluminum silicates and alkali metal silicates.

55. A multicomponent kit for lanthionizing keratin fibers according to claim 54, wherein said alkali metal silicates are chosen from sodium silicate, lithium silicate, and potassium silicate.

56. A multicomponent kit for lanthionizing keratin fibers according to claim 51, wherein said silicates are chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, and phillipsite.

57. A multicomponent kit for lanthionizing keratin fibers according to claim 20, wherein said at least one cation exchange composition is present in an amount ranging from 1% to 50% relative to the total weight of said composition formed upon mixing said first composition and said second composition.

58. A method for lanthionizing keratin fibers to achieve relaxation of said keratin fibers comprising:
(a) generating hydroxide ions comprising combining water, at least one multivalent metal hydroxide, and at least one activating composition comprising at least one cation exchange composition, wherein said at least one cation exchange composition is chosen from zeolites,
(b) applying a composition comprising said generated hydroxide ions to keratin fibers for a sufficient period of time to lanthionize said keratin fibers, and
(c) terminating said lanthionization when a desired level of relaxation of said keratin fibers has been reached.

59. A method for lanthionizing keratin fibers according to claim 58, wherein said keratin fibers are human hair.

60. A method for lanthionizing keratin fibers according to claim 58, wherein said at least one multivalent metal hydroxide is calcium hydroxide.

61. A method for lanthionizing keratin fibers according to claim 58, wherein said zeolites are chosen from zeolite clays.

62. A method for lanthionizing keratin fibers according to claim 58, wherein said zeolites are chosen from analcime, chabazite, gmelinite, harmotome, levynite, mordenite, epistilbite, heulandite, natrolite, stilbite, edingtonite, mesolite, scolecite, thomosonite, brewsterite, faujasite, gismondine, laumontite, and phillipsite.

63. A method for lanthionizing keratin fibers according to claim 58, wherein said at least one activating composition further comprises at least one complexing agent effective for dissociating said at least one multivalent metal hydroxide.

64. A method for lanthionizing keratin fibers according to claim 63, wherein said at least one complexing agent is chosen from chelating agents and sequestering agents.

* * * * *